(12) United States Patent
Jeon

(10) Patent No.: US 9,775,942 B2
(45) Date of Patent: Oct. 3, 2017

(54) BUFFY COAT EXTRACTION KIT

(71) Applicant: Min-yong Jeon, Seoul (KR)

(72) Inventor: Min-yong Jeon, Seoul (KR)

( * ) Notice: Subject to any disclaimer, the term of this patent is extended or adjusted under 35 U.S.C. 154(b) by 0 days.

(21) Appl. No.: 14/655,340

(22) PCT Filed: Dec. 17, 2013

(86) PCT No.: PCT/KR2013/011739
§ 371 (c)(1),
(2) Date: Jun. 25, 2015

(87) PCT Pub. No.: WO2014/104640
PCT Pub. Date: Jul. 3, 2014

(65) Prior Publication Data
US 2015/0335812 A1    Nov. 26, 2015

(30) Foreign Application Priority Data

Dec. 27, 2012 (KR) .................. 10-2012-0154144
Jul. 15, 2013 (KR) .................. 10-2013-0082619
Aug. 29, 2013 (KR) .................. 10-2013-0102782

(51) Int. Cl.
*A61M 1/36* (2006.01)
*A61J 1/06* (2006.01)
(Continued)

(52) U.S. Cl.
CPC .............. *A61M 1/3693* (2013.01); *A61J 1/06* (2013.01); *B01L 3/5021* (2013.01); *A61J 1/1406* (2013.01);
(Continued)

(58) Field of Classification Search
CPC .......... A61M 1/3693; A61M 2202/0439; A61J 1/06; A61J 1/1406; G01N 33/491;
(Continued)

(56) References Cited

FOREIGN PATENT DOCUMENTS

KR    10-2011-0009651    1/2011
KR    10-2011-0046621    5/2011
(Continued)

OTHER PUBLICATIONS

Translation of the Written Opinion of the International Searching Authority for PCT/KR2013/011739, dated Jun. 27, 2015.*
(Continued)

*Primary Examiner* — David A Reifsnyder

(57) ABSTRACT

The present invention relates to a buffy coat extraction kit including: a kit body having a cylindrical plasma part that has an internal volume for forming a plasma layer, a cylindrical buffy coat part which extends in the longitudinal direction while communicating with the lower part of the plasma part and has a diameter smaller than the diameter of the plasma part and an internal volume for forming a buffy coat layer, and a cylindrical erythrocyte part which extends in the longitudinal direction while communicating with the lower part of the buffy coat part and has a diameter larger than the diameter of the buffy coat part and an internal volume for forming an erythrocyte layer, wherein the free end part of the plasma part and the free end part of the erythrocyte part are respectively opened; a lower packing movably accommodated in the erythrocyte part while maintaining an air-tight state; and a pusher moving the lower packing.

7 Claims, 6 Drawing Sheets

(51) Int. Cl.
*A61J 1/14*     (2006.01)
*B01L 3/00*     (2006.01)
*G01N 33/49*    (2006.01)

(52) U.S. Cl.
CPC .............. *A61M 2202/0427* (2013.01); *A61M 2202/0439* (2013.01); *B01L 2200/0689* (2013.01); *B01L 2300/044* (2013.01); *B01L 2300/0858* (2013.01); *B01L 2400/0478* (2013.01); *G01N 33/491* (2013.01)

(58) Field of Classification Search
CPC ........... B01L 3/5021; B01L 2200/0689; B01L 2300/044; B01L 2300/0858; B01L 2400/0478
See application file for complete search history.

(56) References Cited

FOREIGN PATENT DOCUMENTS

| | | |
|---|---|---|
| KR | 10-1125073 | 3/2012 |
| KR | 10-1128163 | 3/2012 |
| KR | 10-1140551 | 5/2012 |
| KR | 10-2294044 | 10/2012 |
| KR | 10-1208880 | 12/2012 |
| WO | WO 2010/138895 | 12/2010 |
| WO | WO 2014/104640 | 7/2014 |

OTHER PUBLICATIONS

International Search Report Dated May 26, 2014 From the Korean Intellectual Property Office Re. Application No. PCT/KR2013/011739 and its Translation Into English.

\* cited by examiner

BUFFY COAT EXTRACTION KIT

RELATED APPLICATIONS

This application is a National Phase of PCT Patent Application No. PCT/KR2013/011739 having International filing date of Dec. 17, 2013, which claims the benefit of priority of Korean Patent Applications Nos. 10-2013-0102782 filed on Aug. 29, 2013, 10-2013-0082619 filed on Jul. 15, 2013 and 10-2012-0154144 filed on Dec. 27, 2012. The contents of the above applications are all incorporated by reference as if fully set forth herein in their entirety.

TECHNICAL FIELD

The present disclosure relates to a buffy coat extractor apparatus or kit, and more particularly to a buffy coat extraction kit used for extracting buffy coat from a blood collection for the purpose of autologous blood or PRP (Platelet Rich Plasma) cell regeneration treatment and skin regeneration treatment.

BACKGROUND

Separation of biological substance may be classified as the most fundamental operation in biology, genetics and medical science etc. for not only analysis of substance but also cultivation of cells, and identification and amplification of DNA. Frontier medical research is competitively conducted in regenerative medicines using stem cells. The stem cells include embryonic stem cells obtained from blastocyst of initial stage of generation and adult stem cells obtained from adult or placenta whose generation process has been terminated.

The adult stem cells are obtained by three principal methods of: firstly using bone marrow; secondly, umbilical cord blood; and thirdly, peripheral blood (mesenchymal blood) which enables easy harvesting of the adult stem cells. In all these methods, blood is first separated into major components of erythrocyte, leukocyte, blood platelet and blood plasma by means of centrifugation, followed by an operation of separating the stem cell (mononuclear).

In this connection, conventional centrifugation methods may be summarized as follows. When a contained solution of various mixed substances, particularly, collected blood of human being or animal is centrifuged, erythrocyte, leukocyte, blood platelet and other blood plasma in the blood are orderly positioned in layers in the order of weight with the heaviest fraction layered at the bottom of the container due to their inherent difference in specific gravity.

In the initial process of transferring the peripheral blood extracted through syringe needle to the centrifuge container, a stopper of the centrifuge container is opened, the needle of the syringe is positioned inside the centrifuge container, the peripheral blood in the syringe is passed to the centrifuge container, and thereafter the needle is removed from the centrifuge container and the opened centrifuge container is closed with the stopper. The centrifuge container is subsequently positioned in bucket of the centrifugal separator, and the separator is operated by setting desired time, rotational speed (rpm) or acceleration of gravity (g).

The erythrocyte typically has the largest specific gravity among the components of the blood and thus is collected in the bottom portion of the centrifuge container, and the erythrocyte account for 47% of the whole blood for man and 42% for woman. Positioned above the erythrocyte are the leukocyte and blood platelet which account for about 1% of the whole blood, which further includes monocytes or stem cells of the peripheral blood.

The remainder thereabove is serum and fibrinogen referred to as blood plasma. The centrifuge container that completed the centrifugation is recovered and the stopper is then reopened so that a desired substance may be extracted from among the substances separated due to the difference in specific gravity of the component substances, by means of a pipette or capillary tube or needle, and thereafter the remaining components are separately stored or discarded or re-cycled.

In recent times, there has been strong public interest in autologous blood cell regeneration treatment (hereinafter called PRP treatment) which is the collection of PRP from a single patient by way of the aforementioned separation and injection back to the same patient at the lesion where tissue has been damaged to regenerate the tissue, whereby healing the wound. The PRP treatment is widely applied to the field of treatment such as treatment for regenerating the damaged cartilage and treatment for regenerating damaged skin tissue such as acne marks so as to improve the skin condition.

The platelets in the blood and are known to be rich with growth factors, and are also known to cause cell proliferation in the human body, produce collagen, leads to regeneration of angiogenic cells and serves to heal wounds.

One microliter of the human blood contains about 100,000-200,000 or so platelets, and in order for a PRP treatment to be effective, they are concentrated to have 1 million or more counts of platelets per microliter. Such concentration of platelets may be performed through stratifying collected blood by using a centrifugal separator to have typical blood layered with the red blood cells or erythrocytes forming the bottommost layer, a dark yellow buffy coat layer thereon formed of leukocytes and platelets, and pale yellow plasma forming the uppermost layer.

The respective blood layers separated as above are, on average, erythrocyte layer occupying about 45% in volume ratio, the buffy coat layer by 1%, and the plasma layer by 54%. The PRP treatment utilizes the platelet-rich buffy coat layer extracted from the separated blood as described above wherein the mere 1% volume ratio makes it difficult for a conventional blood collection kit to accurately extract the buffy coat alone.

Korean Patent Application Publication No. 10-2010-0116106, entitled "Assembly, device kit and method for preparing platelet-rich plasma" (applicant: Estar Technologies Ltd.) discloses a centrifuge test tube for concentrating platelets of whole blood extracted from a patient to obtain fractions thereof. However, the centrifuge tube in the form of a cylinder with a uniform inner diameter is not apt for accurately extracting the buffy coat fraction only.

Korean Patent Application Publication No. 10-2011-0045980, entitled "Kit of centrifuge separation and methods for centrifuging using the same" (applicant: GLOTECH) discloses collecting whole blood or bodily fluids and then providing a centrifuge separation kit installed with a syringe to undergo centrifugation for immediately collecting target substances such as platelet-rich plasma or stem cells. The centrifuge separation kit still maintains a centrifuge separation tube in the form of a cylinder with a uniform inner diameter, which is susceptible to undesirable accompaniment of separation gel or red blood cells to the target buffy coat during the collection process.

Therefore, Korean Patent Application Publication No. 10-2012-0089723 filed by the present applicants discloses a centrifuge tube provided with a narrowed chamber for separately forming buffy coat therein and at least one rib at an upper chamber and at an intermediate chamber to prevent lateral fluid movements from occurring especially in fixed angle centrifuges and thereby separates substances in the tube accurately. However, the centrifuge tube lacks a means for controlling the buffy coat layer once it is received in a lower chamber of the tube.

Furthermore, the conventional separator kits have caps that involve manual uncapping, injection of blood from a syringe and then recapping with a human hand, which is seriously insanitary and leaves the blood susceptible to contamination through airborne infection.

DISCLOSURE

Technical Problem

Therefore, the present disclosure in at least one embodiment seeks to provide a buffy coat extraction kit capable of extracting platelet-rich buffy coat more easily from blood fractions through a centrifuge for the purpose of easier separation of biological substance and more particularly of the state of the art PRP treatment.

In addition, a buffy coat extraction kit according to at least one embodiment of the present disclosure enables a buffy coat layer to be easily distinguished and accurately extracted from the centrifuged blood.

Further, a buffy coat extraction kit according to at least one embodiment of the present disclosure takes account of varying composition ratios of the red cells, buffy coat and plasma of even a single person depending on the person's health condition at the time of the blood collection, to which the buffy coat is repositioned to the optimal place allowing more accurate extraction thereof.

Additionally, a buffy coat extraction kit according to at least one embodiment of the present disclosure obviates the need for a manual opening or closing the extractor during its operation to prevent the extractor or the substances from being contaminated by human touches.

A buffy coat extraction kit according to at least one embodiment of the present disclosure minimizes lateral movements of the extractor apparatus during the centrifugal operation to prevent disturbances from occurring in the buffy coat layer and thereby provides more accurate centrifuge.

SUMMARY OF THE INVENTION

The present disclosure in some embodiments provides a buffy coat extraction kit including a kit main body, an erythrocyte section, a lower gasket and a pusher. The kit main body includes: a plasma section having a cylindrical shape and an internal volume which forms a plasma layer; a buffy coat section having a cylindrical shape and a diameter smaller than that of the plasma section, extending longitudinally from and communicating with a lower portion of the plasma section, and having an internal volume which forms a plasma layer; and an erythrocyte section having a cylindrical shape and a diameter greater than that of the buffy coat section, extending longitudinally from and communicating with a lower portion of the buffy coat section, and having an internal volume which forms an erythrocyte layer. The plasma section and the erythrocyte section respectively have openings formed at free distal ends. The lower gasket is received movably under an air-tight sealing within the erythrocyte section. The pusher is configured to move the lower gasket.

Here, the buffy coat extraction kit may further include an upper gasket provided in the plasma section and configured to close the opening of the plasma section; and an upper cap coupled to the opening of the plasma section.

The buffy coat extraction kit may further include a lower cap defining a passage for allowing the pusher to pass through and configured to engage the opening of the erythrocyte section for holding the lower gasket from falling off the erythrocyte section.

The lower gasket may be threadedly coupled or press fitted with the pusher.

The lower gasket may include a connector to which the pusher is removably coupled, and a sealing member coupled to the connector in close contact with an inner peripheral surface of the erythrocyte section for keeping the erythrocyte section air-tight sealed.

The connector may be formed with a retaining groove depressed circumferentially on an outer peripheral surface of the connector and configured to retain the sealing member.

At least one of the plasma section and the buffy coat section may have a supporting rib protruding from outer peripheral surfaces of the kit main body in the longitudinal direction of the kit main body or in the lateral direction with respect to the longitudinal direction of the kit main body.

The lower gasket and the pusher may be formed integrally.

Advantageous Effects

The buffy coat extraction kit according to at least one embodiment of the present disclosure has a buffy coat section arranged to form a substantially elevated buffy coat layer by even 1% of trace amount of whole blood as treated by the centrifuge so as to enable the operator to identify the buffy coat by the naked eye and accurately extract the same by using a syringe.

Additionally, even with some blood having a non-uniform composition ratio of red blood cells, bully coat and plasma, an embodiment of the present disclosure has a lower gasket elevated for moving the buffy coat layer into the buffy coat section so as to enable the operator to identify the buffy coat by the naked eye and accurately extract the same by using a syringe.

Furthermore, the buffy coat extraction kit according to at least one embodiment of the present disclosure can prolong the retention time of buffy coat by adopting a closed system requiring no capping and uncapping but a brief disinfection with alcohol cotton or the like before injection of blood or extraction of buffy coat and thereby precludes possible contaminations with the conventional method that involves handling of the extractor cap by hand transmitting bacteria directly to the blood or airborne infection during its capping and uncapping operation.

Furthermore, the buffy coat extraction kit is provided with supporting ribs and supporting protrusions for providing an accurate extraction of buffy coat by preventing minute lateral slopping of the blood fractions during the centrifuge operation, deformation of the extractor apparatus due to high gravitational acceleration, and uncontrolled dispersion of buffy coat.

The buffy coat extraction kit may be further provided with a pusher configured to provide a gradual rotational elevation of the buffy coat to be present securely within the buffy coat section.

A lower gasket takes advantage of the gravitational load generated by the centrifugation to maintain a strong adherence of the lower gasket for preventing the blood from leaking due to the centrifugation.

REFERENCE NUMERALS

Figure 1:
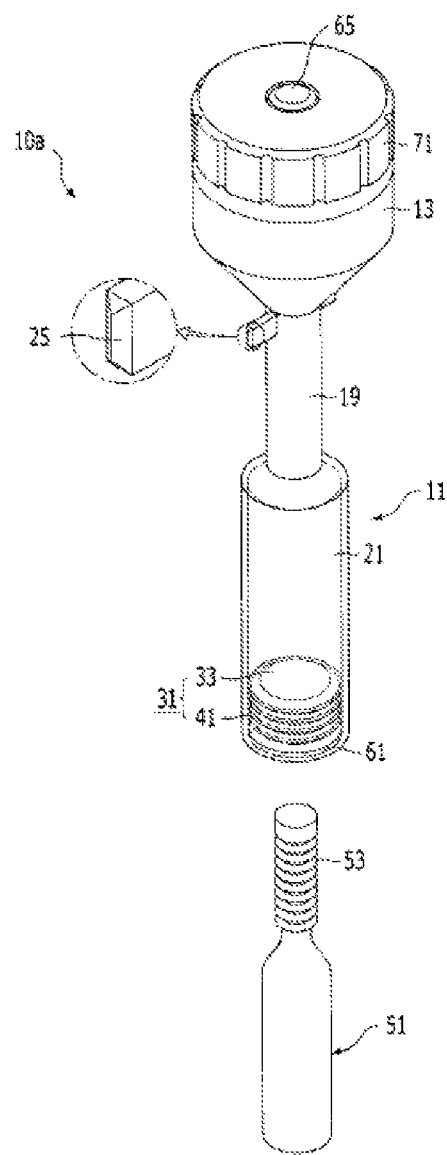
FIG. 1 is a perspective view of a buffy coat extractor kit according to a first embodiment of the present disclosure.

| 11: kit main body | 13: plasma section |
|---|---|
| 19: buffy coat section | 21: erythrocyte section |
| 25: supporting rib | 31: lower gasket |
| 33: connector | 41: sealing member |
| 51: pusher | 61: lower cap |
| 65: upper gasket | 71: upper cap |

DETAILED-DESCRIPTION OF SPECIFIC EMBODIMENTS OF THE INVENTION

Hereinafter, at least one embodiment of the present disclosure will be described in detail with reference to the accompanying drawings.

In the following description, like reference numerals would rather designate like elements although the elements are shown in different drawings with respect to the first embodiment as a representative. Further, in the following description of some other embodiments, a detailed description of other functions and configurations than those of the first embodiment will be presented for the purpose of clarity and for brevity.

The buffy coat extraction kit of at least one embodiment of the present disclosure is adapted to receive an injection of blood, fractionate the blood into an erythrocyte layer, buffy coat layer and plasma layer by using a centrifuge, and thereby extract buffy coat exactly from the buffy coat layer.

Figure 2:
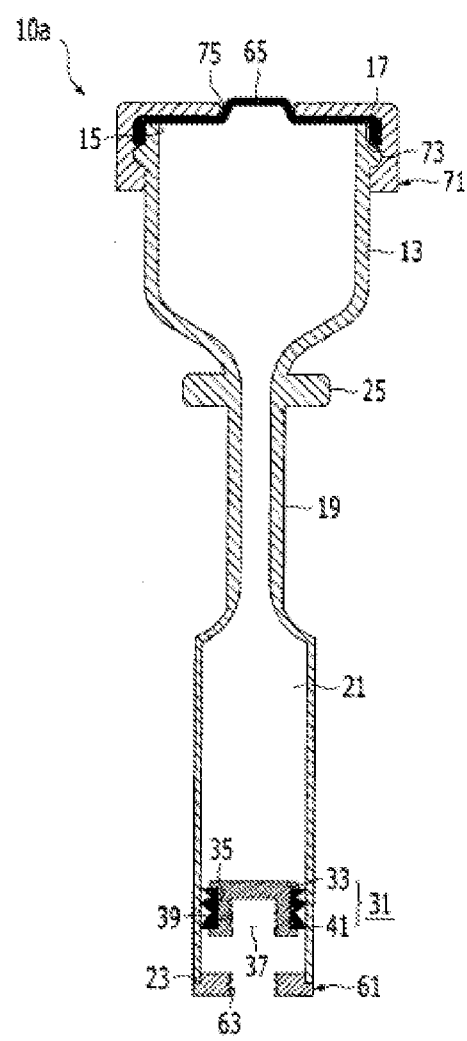
FIG. 2 is a cross sectional view of the buffy coat extractor kit of FIG. 1.

As shown in FIGS. 1 and 2, the buffy coat extraction kit 10a according to the first embodiment of the present disclosure includes a kit main body 11, a lower gasket 31 and a pusher 51.

To serve as a blood container, the kit main body 11 has a hollow cylindrical shape made of a transparent resin and includes a plasma section 13, a buffy coat section 19 and an erythrocyte section 21.

The plasma section 13 is where the plasma in the blood is collected when the blood is centrifuged, and it has an internal volume which forms the plasma layer 5 (see FIG. 6). Formed on the outer circumferential surface of the plasma section 13, for example, on the outer peripheral surface adjacent to an opening 15 of the plasma section 13 is a predetermined protrusion 17 configured to engage a groove 73 on an upper cap 71 which will be described below.

On the other hand, the upper cap 71 may also be threadedly coupled to the plasma section 13.

The buffy coat section 19 has a smaller diameter than that of the plasma section 13, communicating with the plasma section 13 at its bottom side. The buffy coat section 19 is elongated and has an internal volume which defines a buffy coat layer 7 (see FIG. 6).

The erythrocyte section 21 is adapted to be directly inserted into a centrifuge bucket (not shown) and it has a diameter larger than that of the buffy coat section 19, communicating with the buffy coat section 19 at its bottom side. The erythrocyte section 21 is elongated and has an internal volume which defines an erythrocyte layer 9 (see FIG. 6).

Thus, the kit main body 11 is made taking into account the normal blood composition ratio of erythrocytes, buffy coat and plasma with such diameters and lengths of its plasma section 13, buffy coat section 19 and erythrocyte section 21 that a buffy coat layer 7 is formed upon blood centrifugation at the middle portion of the buffy coat section 19 or at least the erythrocyte section 21. The plasma section 13 and the erythrocyte section 21 have openings 15 and 23 formed at their free ends, respectively. In addition, the kit main body 11 has its plasma section 13, buffy coat section 19 and erythrocyte section 21 interconnected through gradually changing diameters to facilitate flowing of blood inside the kit main body 11.

Meanwhile, the buffy coat extraction kit 10a according to the first embodiment of the present disclosure has the erythrocyte section 21 with a smaller diameter than that of the plasma section 13. Typically, the larger amount of blood introduced, the more buffy coat is obtained after the present buffy coat extraction kit 10a is inserted in a bucket for corotation. As long as the buffy coat extraction kit 10a fits the specified internal volume of the bucket, the remaining plasma section 13 is free to have an extended diameter. In this case, the buffy coat extraction kit 10a is formed unproportionate, for example, having the plasma section 13 overhang the erythrocyte section 21 to worsen lateral wobbling during the operation of the centrifuge, which causes the minute quantity of buffy coat layer 7 to be shakingly dispersed and thus hinders to precisely collect and extract the buffy coat.

The first embodiment provides the buffy coat section 19 on its outer peripheral surface with a supporting rib 25 in order to prevent the kit main body 11 from damage or deformation due to high gravitational acceleration applied thereto by the centrifuge operation while minimizing the lateral wobbling of the buffy coat extraction kit 10a. The supporting rib 25 protrudes with a constant width in the lateral direction from the outer peripheral surface of the buffy coat section 19 with respect to the longitudinal direction of the kit main body 11, but it is not limited thereto in that the supporting rib 25 may be formed protruding longitudinally of the outer peripheral surface of the buffy coat section 19. In addition, the supporting rib 25 may be formed protruding from the outer peripheral surface of the plasma section 13 in the longitudinal direction or latitudinal direction of the kit main body 11. The supporting rib 25 may also be formed on the outer peripheral surfaces of the plasma section 13 and the buffy coat section 19 to reach inner peripheral surfaces of the bucket. This makes the buffy coat extraction kit 10a interoperable among somewhat different buckets of centrifuges from different manufactures, wherein slightly smaller buckets can slidably receive the buffy coat extraction kit 10a easily with slight additional forces while slightly larger buckets can receive the same with increased tightness therebetween to prevent the lateral wobbling of the buffy coat extraction kit 10a during the rotational operation of the centrifuge, whereby avoiding a disturbance of the buffy coat layer 7.

Lower gasket 31 is movably accommodated in the erythrocyte section 21 with an air-tight sealing maintained therebetween. That is, the lower gasket 31 is provided within the erythrocyte section 21 to advance along the length of the kit main body 11, having its outer peripheral surface in close contact with the inner circumferential surface of the kit main body 11.

The lower gasket 31 includes a connector 33 to which the pusher 51 is removably coupled, and a sealing member 41 coupled to the connector 33 in close contact with the inner peripheral surface of the erythrocyte section 21 for keeping the erythrocyte section air-tight sealed.

Connector 33 is formed with a retaining groove 35 depressed at a predetermined depth circumferentially on the outer peripheral surface of the connector 33. The inner peripheral surface of the connector 33 is formed with a socket groove 37 to which the pusher 51 is detachably attached. In this embodiment, a female thread 39 is formed on the inner peripheral surface of the socket groove 37 of the connector 33.

Also provided is a ring-shaped sealing member 41 made of an elastic material. The sealing member 41 is seated on the retaining groove 35 of the connector 33 and is firmly coupled with the connector 33. The outer peripheral surface of the sealing member 41 is formed with, but not limited to, irregularities, and it may also be planar.

The pusher 51 is detachably attached to the socket groove 37 of the connector 33 of the lower gasket 31, and the pusher 51 coupled to the socket groove 37 may move in unison with the lower gasket 31 toward the buffy coat section 19. The end portion of the pusher 51, which is coupled to the socket groove 37 of the connector 33, is formed with a male thread 53 matching the female thread 39 of the socket groove 37 so that the pusher 51 may gradually lift the lower gasket 31 longitudinally of the kit main body 11 by threadedly coupling the pusher 51 to the lower gasket 31.

In the embodiment described above, the lower gasket 31 is constituted by the connector 33 and the sealing member 41 and the pusher 51 is detachably attached to the connector 33 of the lower gasket 31, which is not so limited but the lower gasket 31 may be made of the same elastic material as the sealing member 41 and the lower gasket 31 may be formed integrally with the pusher 51.

In addition, the first embodiment buffy coat extraction kit 10a according to the present disclosure includes a lower cap 61 that engages the opening 23 of the erythrocyte section 21 for holding the lower gasket 31 from falling off the erythrocyte section 21. The lower cap 61 is formed with a passage 63 for allowing the pusher 51 to pass therethrough.

The lower cap 61 is formed to have a diameter no greater than the outer diameter of the erythrocyte section 21. This maximizes the outer diameter of the erythrocyte section 21 to be as close as to the inner diameter of the bucket to secure the most possible space in the erythrocyte section 21 for containing the blood, resulting in maximized harvesting of buffy coat even with a small centrifuge.

Such lower cap 61 may be either removably attached to the opening 23 of the erythrocyte section 21 or fused thereto by a method such as ultrasonic welding.

In addition, the buffy coat extraction kit 10a according to the first embodiment of the present disclosure includes an upper gasket 65 for closing the opening 15 of the plasma section 13 and an upper cap 71 adapted to receive the upper gasket 65 and mate with the opening 15 of the plasma section 13.

The upper gasket 65 is made of a soft material such as silicone for allowing the needle 3 of a syringe 1 (see FIG. 6) to easily pass through while keeping the extraction kit 10a sealed.

The inner peripheral surface of the upper cap 71 is circumferentially depressed into a circumferential groove 73 which the protrusion 17 of the plasma section 13 locks into.

The upper cap 71 is centrally formed with a bore 75 through which the upper gasket 65 is partially exposed. In the present embodiment, the partially exposed area of the upper gasket 65 projects upward convexedly to be press fitted into the bore 75 of the upper cap 71. The protrusion of the exposed convex portion of the upper gasket 65 coupled with the bore 75 facilitates preparative disinfection thereof with, for example, alcohol or Betadine. In this embodiment, the exposed portion of the upper gasket 65 is described as being protruded as a convex, although it is not limited thereto. The exposed portion of the upper gasket 65 may be formed to lie flush with the opening 15 and block the bore 75.

Thus, the buffy coat extraction kit 10a in accordance with the first embodiment of the present disclosure provides a securely enclosed structure by closing the opening 15 of the plasma section 13 with the upper cap 71 and the upper gasket 65 and by sealing the erythrocyte section 21 with the lower gasket 31 so as to protect the overall process through the blood injection and buffy coat extraction from being exposed to external air against deterioration of the blood, which prolongs the shelf life of the blood further.

Figure 3:
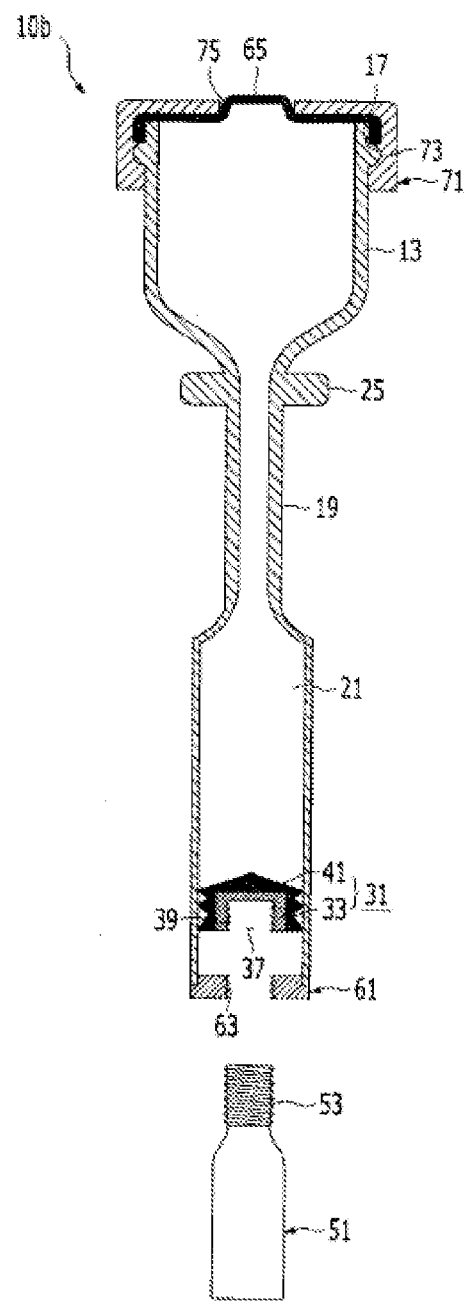
FIG. 3 is a perspective view of a buffy coat extractor kit according to a second embodiment of the present disclosure.

Meanwhile, a buffy coat an extraction kit 10b according to a second embodiment of the present disclosure shown in FIG. 3 differs from the first embodiment described above in that the top portion of the sealing member 41 of the lower gasket 31 has a conical top portion projecting toward the buffy coat section 19.

Figure 4:
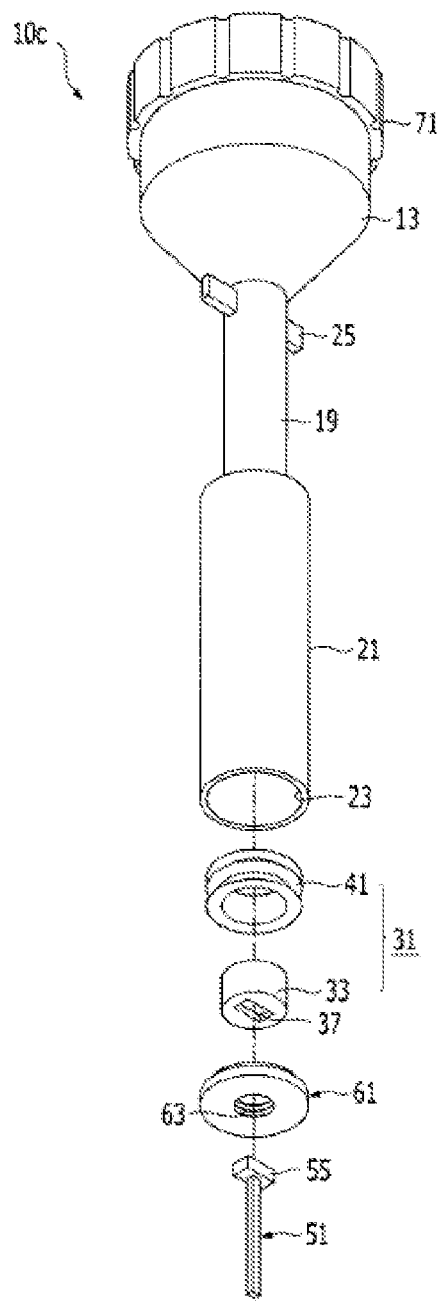
FIG. 4 is a perspective view of a buffy coat extractor kit according to a third embodiment of the present disclosure.

In addition, a buffy coat extraction kit 10c according to a third embodiment of the present disclosure shown in FIG. 4 is similar to the first embodiment described above except that the lower gasket 31 and the pusher 51 are configured to be press fitted rather than threadedly fastened.

To this end, the socket groove 37 on the connector 33 of the buffy coat extraction kit 10c according to the third embodiment is formed as a depression having a square cross section, and in response, the pusher 51 is distally formed with a lug 55 protruding into square cross-sectional shape.

Thus, the pusher 51 may be press fitted by the lug 55 into the socket groove 37 on the connector 33 before gradually lifting the lower gasket 31 longitudinally of the kit main body 11.

Figure 5:
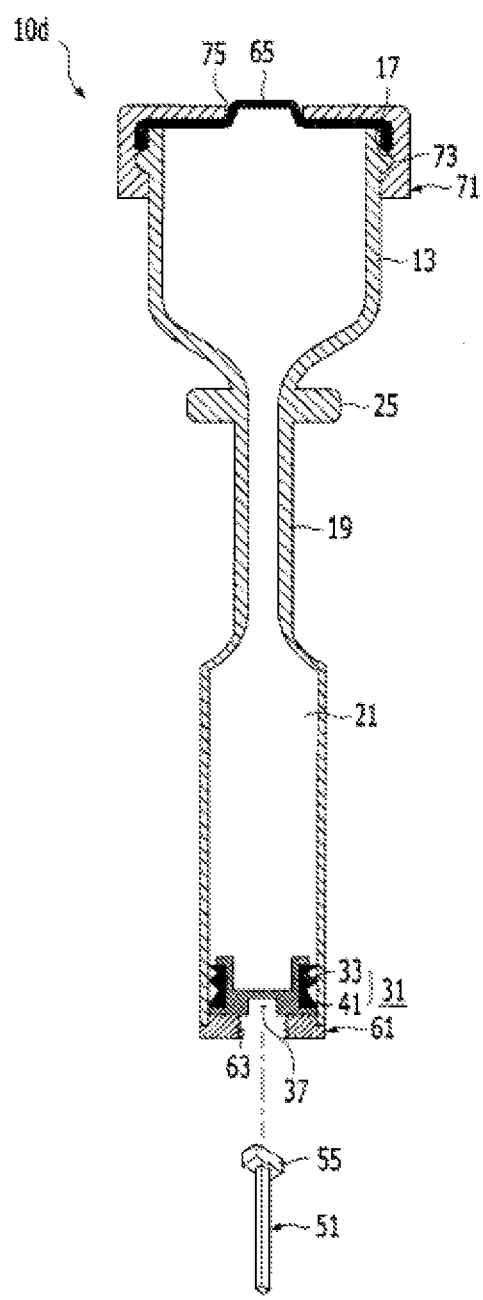
FIG. 5 is a perspective view of a buffy coat extractor kit according to a fourth embodiment of the present disclosure.

Furthermore, a buffy coat extraction kit 10d according to a fourth embodiment of the disclosure shown in FIG. 5 is similar to the third embodiment described above except that the shape of the top of the connector 33 is depressed.

With such a configuration, the following will describe a method for extracting buffy coat from blood based on the first buffy coat extraction kit 10a as a representative example among other embodiments.

Figures 6A, 6B, 6C, 6D:
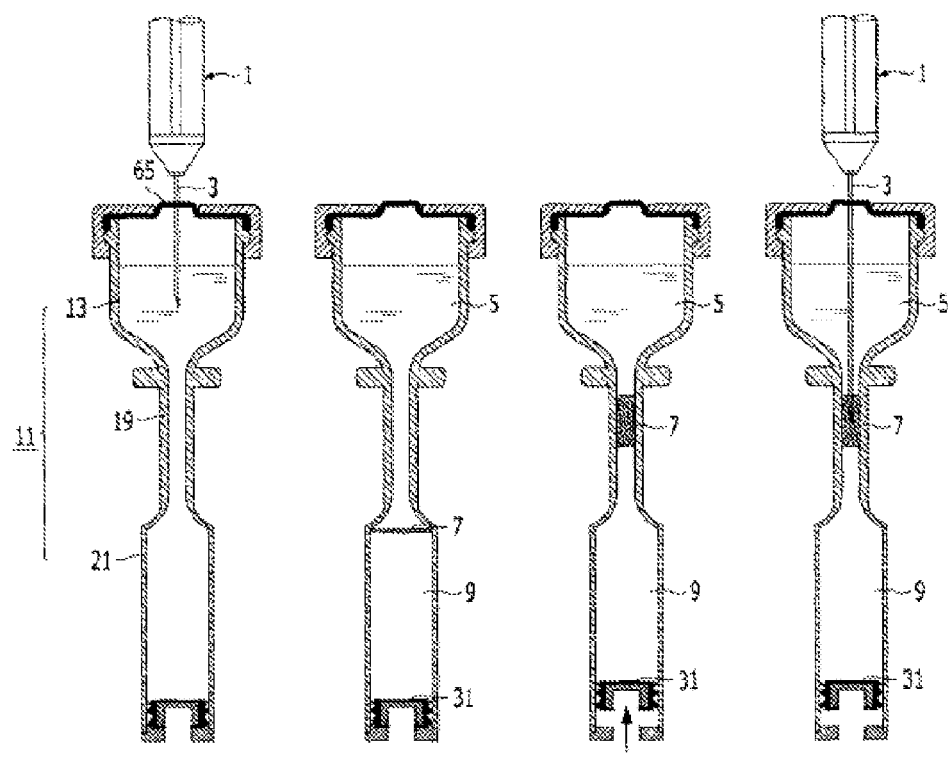
FIGS. 6A-6D are diagrams of steps for extracting buffy coat from a blood sample collected by using buffy coat extractor kit according to the first embodiment of the present disclosure.

First, after disinfecting the exposed portion of the upper gasket 65 with an alcohol pad or the like, the needle 3 of the syringe 1 as shown in FIG. 6(a) pierces through the upper gasket 65 of the syringe 1 and then injects the blood sample to be centrifuged into the buffy coat extraction kit 10a before removing the syringe 1.

Thereafter, the bully coat extraction kit 10a containing the injected blood is loaded into the bucket of the centrifuge to separate the blood into layers including the plasma layer 5, buffy coat layer 7 and erythrocyte layer 9 in this order.

The centrifuged laminar separation performed in this way on an ordinary blood typically forms the bully coat layer 7 at a location in the erythrocyte section 21 deviated from the buffy coat section 19, as shown in FIG. 6(b).

If the bully coat layer 7 is formed in the erythrocyte section 21, the bully coat layer 7 is relocated to the narrower bully coat section 19 by lifting the lower gasket 31 through the pusher 51 as shown in FIG. 6(c), whereby rendering the buffy coat layer 7 to be easily visible.

Then, as shown in FIG. 6(d), the tip of the needle 3 of the syringe 1 pierces through the exposed region of the upper gasket 65 to reach the buffy coat layer 7 so as to extract the bully coat.

The method of extracting buffy coat by using the extraction kit 10a as described above achieves very accurate separation of buffy coat, which leads to harvesting a high quality PRP (Platelet Rich Plasma).

According to some embodiments of the present disclosure as described above, a buffy coat extraction kit is configured with a plasma section, buffy coat section and erythrocyte section in which a lower gasket is received movably to variable positions under control through a pusher so that the lower gasket may be elevated to reposition the buffy coat layer of blood into the buffy coat section where the naked eye can identify the precise buffy coat to extract by using a syringe even if the blood happens to have a non-uniform composition ratio of red blood cells, buffy coat and plasma.

Furthermore, the buffy coat extraction kit according to at least one embodiment of the present disclosure prolongs the retention time of buffy coat by adopting a closed system requiring no capping and uncapping but a brief disinfection with alcohol cotton or the like before injection of blood or extraction of buffy coat and thereby precludes possible contaminations with the conventional method that involves handling of the extractor cap by hand transmitting bacteria directly to the blood or airborne infection during its capping and uncapping operation.

Furthermore, the buffy coat extraction kit is provided with supporting ribs and supporting protrusions for providing an accurate extraction of buffy coat by preventing minute lateral slopping of the blood fractions during the centrifuge operation, deformation of the extractor apparatus due to high gravitational acceleration, and uncontrolled dispersion of buffy coat.

The buffy coat extraction kit may be further provided with a pusher configured to provide a gradual rotational elevation of the buffy coat to be present securely within the buffy coat section.

A lower gasket takes advantage of the gravitational load generated by the centrifugation to maintain a strong adherence of the lower gasket for preventing the blood from leaking due to the centrifugation.

What is claimed is:

1. A buffy coat extraction kit, comprising:
   a kit main body comprising:
      a plasma section having a cylindrical shape and an internal volume which forms a plasma layer,
      a buffy coat section having a cylindrical shape and a diameter smaller than that of the plasma section, extending longitudinally from and communicating with a lower portion of the plasma section, and having an internal volume which forms a plasma layer,
      an erythrocyte section having a cylindrical shape and a diameter greater than that of the buffy coat section, extending longitudinally from and communicating with a lower portion of the buffy coat section, and having an internal volume which forms an erythrocyte layer, and
      the plasma section and the erythrocyte section respectively having openings formed at free distal ends;
   a lower gasket received movably under an air-tight sealing within the erythrocyte section;
   a pusher configured to move the lower gasket; and
   a lower cap defining a passage for allowing the pusher to pass through and configured to engage the opening of the erythrocyte section for holding the lower gasket from falling off the erythrocyte section.

2. A buffy coat extraction kit, comprising:
   a kit main body comprising:
      a plasma section having a cylindrical shape and an internal volume which forms a plasma layer,
      a buffy coat section having a cylindrical shape and a diameter smaller than that of the plasma section, extending longitudinally from and communicating with a lower portion of the plasma section, and having an internal volume which forms a plasma layer,
      an erythrocyte section having a cylindrical shape and a diameter greater than that of the buffy coat section, extending longitudinally from and communicating with a lower portion of the buffy coat section, and having an internal volume which forms an erythrocyte layer, and
      the plasma section and the erythrocyte section respectively having openings formed at free distal ends;
   a lower gasket received movably under an air-tight sealing within the erythrocyte section; and
   a pusher configured to move the lower gasket;
   wherein at least one of the plasma section and the buffy coat section has a supporting rib protruding from outer peripheral surfaces of the kit main body in the longitudinal direction of the kit main body or in the lateral direction with respect to the longitudinal direction of the kit main body.

3. The buffy coat extraction kit of claim 2, further comprising:
   an upper gasket provided in the plasma section and configured to close the opening of the plasma section; and
   an upper cap coupled to the opening of the plasma section.

4. The buffy coat extraction kit of claim 2, wherein the lower gasket is threadedly coupled or press fitted with the pusher.

5. The buffy coat extraction kit of claim 2, wherein the lower gasket comprises:
   a connector to which the pusher is removably coupled; and
   a sealing member coupled to the connector in close contact with an inner peripheral surface of the erythrocyte section for keeping the erythrocyte section airtight sealed.

6. The buffy coat extraction kit of claim 5, wherein the connector is formed with a retaining groove depressed circumferentially on an outer peripheral surface of the connector and configured to retain the sealing member.

7. The buffy coat extraction kit of claim 2, wherein the lower gasket and the pusher are formed integrally.

* * * * *